US009447246B2

(12) United States Patent
Volz et al.

(10) Patent No.: US 9,447,246 B2
(45) Date of Patent: *Sep. 20, 2016

(54) METHOD OF COVALENTLY BONDING AN ORGANIC METAL COMPLEX TO A POLYMER

(75) Inventors: Daniel Volz, Karlsruhe (DE); Tobias Grab, Karlsruhe (DE); Thomas Baumann, Karlsruhe (DE); Michael Bächle, Karlsruhe (DE)

(73) Assignee: CYNORA GMBH, Bruchsal (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/131,622

(22) PCT Filed: Jul. 9, 2012

(86) PCT No.: PCT/EP2012/063447
§ 371 (c)(1),
(2), (4) Date: Jan. 8, 2014

(87) PCT Pub. No.: WO2013/007710
PCT Pub. Date: Jan. 17, 2013

(65) Prior Publication Data
US 2014/0142259 A1    May 22, 2014

(30) Foreign Application Priority Data

Jul. 8, 2011 (EP) .................................. 11173374
Jul. 22, 2011 (EP) .................................. 11175125

(51) Int. Cl.
*C08G 79/14* (2006.01)
*C07F 1/08* (2006.01)
(Continued)

(52) U.S. Cl.
CPC ................ *C08G 79/14* (2013.01); *C07F 1/08* (2013.01); *C07F 9/587* (2013.01); *C08F 8/30* (2013.01);
(Continued)

(58) Field of Classification Search
CPC ...... C08G 79/14; H05B 33/14; H01L 51/009
USPC ........................................................ 525/539
See application file for complete search history.

(56) References Cited

U.S. PATENT DOCUMENTS 4,360,654 A * 11/1982 Hechtl ................. C07F 7/2252
528/18
4,647,680 A * 3/1987 Barfurth ................ C07F 7/006
427/126.1

(Continued)

FOREIGN PATENT DOCUMENTS

CN  201280023097.7   3/2015
DE        3337100 A1   5/1985

(Continued)

OTHER PUBLICATIONS

International Search Report and Written Opinion of International Searching Authority for PCT/EP2012/063447 dated Oct. 19, 2012.

(Continued)

*Primary Examiner* — Mike M Dollinger
(74) *Attorney, Agent, or Firm* — Ryan, Mason & Lewis, LLP

(57) ABSTRACT

The invention relates to a method for covalently bonding an organic metal complex to a polymeric matrix. The method comprises the performance of a first reaction, which comprises a first reactant in the form of an organic metal complex and a second reactant in the form of a polymer, where during the reaction the metal complex is covalently bound to the polymer. According to the invention, the metal complex catalyzes the reaction.

5 Claims, 4 Drawing Sheets

(51) Int. Cl.
| | |
|---|---|
| H01L 51/00 | (2006.01) |
| H05B 33/14 | (2006.01) |
| C08F 12/26 | (2006.01) |
| C08F 212/08 | (2006.01) |
| C08F 212/14 | (2006.01) |
| C08F 8/30 | (2006.01) |
| C08F 8/40 | (2006.01) |
| C08F 8/42 | (2006.01) |
| C09K 11/06 | (2006.01) |
| C07F 9/58 | (2006.01) |
| H01L 51/50 | (2006.01) |

(52) U.S. Cl.
CPC . *C08F 8/40* (2013.01); *C08F 8/42* (2013.01); *C08F 12/26* (2013.01); *C08F 212/08* (2013.01); *C08F 212/14* (2013.01); *C09K 11/06* (2013.01); *H01L 51/004* (2013.01); *H01L 51/009* (2013.01); *H01L 51/0091* (2013.01); *H05B 33/14* (2013.01); C09K 2211/188 (2013.01); H01L 51/0043 (2013.01); H01L 51/5016 (2013.01); Y02E 10/549 (2013.01)

(56) References Cited

U.S. PATENT DOCUMENTS

| | | | | |
|---|---|---|---|---|
| 5,395,887 | A * | 3/1995 | Gondard | C08G 18/838 525/123 |
| 7,858,724 | B2 * | 12/2010 | Kanitz | C07F 15/0033 528/394 |
| 2004/0247934 | A1 | 12/2004 | Takeuchi et al. | |
| 2005/0196637 | A1 | 9/2005 | Herron | |
| 2006/0269779 | A1 | 11/2006 | Takahashi et al. | |
| 2011/0089411 | A1 * | 4/2011 | Xia | H01L 51/002 257/40 |
| 2012/0267612 | A1 * | 10/2012 | Xia | C08G 61/12 257/40 |

FOREIGN PATENT DOCUMENTS

| | | |
|---|---|---|
| DE | 69021559 T2 | 1/1996 |
| EP | 0050358 A2 | 10/1981 |
| EP | 0190998 A1 | 1/1986 |
| WO | 03072584 A1 | 9/2003 |
| WO | 2005042550 A1 | 5/2005 |
| WO | 2010082924 A1 | 7/2010 |
| WO | 2010149748 A1 | 12/2010 |
| WO | 2011067401 A1 | 6/2011 |

OTHER PUBLICATIONS

N. Holten-Andersen et al., "pH-Induced Metal-Ligand Cross-Links Inspired by Mussel Yield Self-Healing Polymer Networks with Near-Covalent Elastic Moduli," Proceedings of the National Academy of Sciences (PNAS), Feb. 2011, pp. 2651-2655, vol. 108, No. 7.

M.P. Garcia Armada et al., "Electrochemical and Bioelectrocatalytical Properties of Novel Block-Copolymers Containing Interacting Ferrocenyl Units," Journal of Organometallic Chemistry, 2008, pp. 2803-2811, vol. 693, No. 16.

B. Ma et al., "Multifunctional Crosslinkable Iridium Complexes as Hole Transporting/Electron Blocking and Emitting Materials for Solution-Processed Multilayer Organic Light-Emitting Diodes," Advanced Functional Materials, Apr. 2009, pp. 1024-1031, vol. 19, No. 7.

D. Volz et al., "Auto-Catalysed Crosslinking for Next-Generation OLED-Design," Journal of Materials Chemistry, Sep. 2012, pp. 20786-20790, vol. 22, No. 38.

Riedl/Janiak, "Anorganische Chemie," XP-002666355, 2007, p. 306.

D. Zink et al., Experimental and Theoretical Study of Novel Luminescent Di-, Tri-, and Tetranuclear Copper Triazole Complexes, ACS Publications, 2011, p. 3275-3283.

D. Liu et al., "Triazole-Based Monophosphines for Suzuki-Miyaura Coupling and Amination Reactions of Aryl Chlorides," ACS Publications, 2005, p. 4907-4910.

L.I. Goryunov et al., "Reaction of Chloropentafluorobenzene and 2,3- and 2,6-Difluoro-bromobenzenes with Lithium Dimethylphosphide," Russian Journal of Organic Chemistry, vol. 45, No. 12, 2009, p. 1859-1861.

* cited by examiner distribution around the most frequent value in nm,
relative position of the graph at random

METHOD OF COVALENTLY BONDING AN ORGANIC METAL COMPLEX TO A POLYMER

FIELD OF INVENTION

The invention relates in particular to a method for covalently binding an organic metal complex to a polymer (a polymeric matrix). The organic metal complex comprises at least one metal center and at least one organic ligand. The method comprises the performance of a first reaction, which comprises a first reactant in the form of an organic metal complex and a second reactant in the form of a polymer, wherein during the reaction the metal complex is covalently bound to the polymer.

BACKGROUND OF THE INVENTION

Due to their properties, phosphorescent transition metal complexes become more and more important as highly efficient emitters in optoelectronic components such as OLEDs. The spin-orbit coupling induced by the transition metal atom (heavy metal atom) results in an increased intersystem-crossing rate from the excited singlet state to the triplet state and thus in the use of the singlet excitons as well as the triplet excitions for emission and thereby allows a theoretical achievable internal quantum yield of 100%.

These phosphorescent dyes are usually introduced into appropriate energetically adjusted host materials. Polymeric structures are particularly suitable for this purpose due to the ease of processing by liquid processing from solution. Ideally, these should fulfill additional functions such as the spatial separation of the dye molecules to prevent undesirable concentration quenching processes and triplet-triplet-annihilation under emission reduction, increased charge carrier injection and transport and an increased recombination probability directly on the emitter molecules.

Thus, the combination of suitable polymeric host structures with appropriate statistically blended emitter compounds and additionally inserted charge transport molecules represents a method diversely used for the preparation of polymeric light emitting diodes (PLEDs). Even though the OLED components produced this way have mostly high efficiencies, these mixed systems can be subject to undesired phase separations, aggregations or crystallization processes, which have a negative effect on the capacity and the lifetime of the components. Therefore, the production of adapted (co)polymers, which fulfill additional functions such as charge transport and emission while at the same time using the advantages of liquid processing, is of steadily increasing interest.

For the synthesis of phosphorescent polymers with directly attached transition metal complexes the subsequent connection of the metal complexes to previously synthesized polymers provided with functional groups ("complexation to the polymer") is known in the art. The optimizing such connection reactions is desirable.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
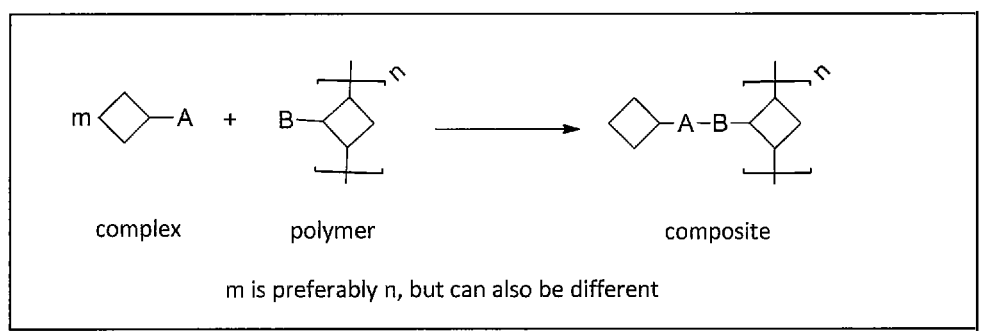
FIG. 1 shows the general scheme for the linkage of organic metal complexes (first reactant) with a polymer (second reactant), each carrying a corresponding anchor group which enables the bonding and optionally the cross-linking of the metal complex in accordance with an embodiment of the present invention.

Exemplary embodiments of the invention will now be discussed in further detail. This invention may, however, be embodied in many different forms and should not be construed as limited to the embodiments set forth herein.

The invention relates in a first aspect to a method for the connection of an organic metal complex to a polymer by the formation of covalent bonds. Here, covalent means a bond between non-metal elements (C, H, N, S, P, O, Si). The organic metal complex comprises at least one metal center and at least one organic ligand, wherein the binding of the metal complex to the matrix is carried out via at least one ligand.

The method comprises the conduction of a first reaction, which comprises a first reactant in the form of an organic metal complex and a second reactant in the form of a polymer. During the first reaction the metal complex is covalently bound to the polymer via at least one ligand. According to the invention, this first reaction is catalyzed by the metal complex bound to the polymer. The metal complex is an educt/reactant and at the same time a catalyst.

The metal center of the metal complex is therefore the catalyzing agent of the reaction. Accordingly, the metal center can be Re, Fe, Ru, Os, Co, Rh, Ir, Ni, Pd, Pt, Cu, Ag, Au, Zn, Cd, Hg, Sn and/or Pb, namely in atomic or ionic form, i.e. as a cationic central ion of the metal complex. Preferably, the metal center is Cu. If the first reaction is carried out as a cross-coupling reaction, such as, for example, Suzuki, Stille, Negishi, Kumada, Hiyama, and Sonogashira reaction, the metal center is preferably Pd, Pt, or Ni.

During this first reaction, the metal complex is being covalently bound via at least one ligand to the polymer, wherein this bond can be single-sided or at least double-sided, i.e. a covalent connection of the metal complex via only one ligand to only one polymer molecule can take place or a simultaneous covalent connection of the metal complex via at least two ligands to at least two different polymer molecules can take place, resulting in a cross-linking of the metal complex in the polymer, generating a multi-dimensional network.

In case in an embodiment of the method a multi-dimensional network is formed (cross-linking), this can be in its simplest shape a ladder-like (two-dimensional) structure, in which two polymer molecules are linked by at least one metal complex, which forms via at least two ligands with one of the polymer molecules each at least one covalent bond. Furthermore, as product of the first reaction complicated three-dimensional networks are possible, which comprise metal complexes cross-linked with a variable number of polymeric molecules. The cross-linked metal complex is thus immobilized in the multi-dimensional network.

For the covalent linking of the organic metal complex to the second reactant different strategies are available. Thereby, pairs of corresponding chemical groups, which can form a covalent chemical bond with each other, are usually used. These chemical groups which are also referred to herein as anchor groups, belong to a first anchor group species or to a second anchor group species, wherein the anchor groups of the first anchor group species can form a covalent bond with the anchor groups of the second anchor group species. However, anchor groups of a first anchor groups species cannot form a covalent bond among themselves and anchor groups of a second anchor group species cannot form a covalent bond among themselves.

In the following, at first the single-sided linking (A) and then the double-sided linking (cross-linking) will be explained.

A. According to a first strategy of the single-sided covalent linking of the organic metal complex to the second reactant, the ligand of the metal complex comprises an anchor group of a first anchor group species, which serves for the covalent binding of the metal complex via the ligand to the polymer. The second reactant comprises at least one anchor group of a second anchor group species, which is suitable for the binding of the second reactant to the anchor group of the ligand of the metal complex. The binding of the metal complex to the polymer results from the reaction of the anchor groups of the ligands of the metal complex with a second anchor group of a second reactant.

According to a second strategy of the single-sided covalent linking of the organic metal complex to the second reactant, a third reactant, which can also be named "spacer" molecule, takes part in the first reaction.

Thereby, the ligand of the metal complex comprises an anchor group of a first anchor group species, which is suitable for the covalent integration of the metal complex via the ligand into the matrix by a second anchor group. The second reactant comprises an anchor group of a first anchor group species, which serves for the binding of the second reactant to a second anchor group, so that the metal complex cannot bind directly to the second reactant. For the formation of a covalent bond between the ligand of the metal complex and the second reactant a third reactant is added, which comprises two anchor groups of a second anchor group species, wherein each of these anchor groups of the third reactant can form a covalent bond with one first anchor group each (namely of the metal complex and of the second reactant). Thus, the binding of the metal complex to the polymer takes place via the ligand by reaction of the anchor group of the ligand of the metal complex and by reaction of the anchor group of the second reactant with the same third reactant, so that a binding of the metal complex to the polymer results.

B. According to a first strategy of the double-sided covalent linking of the organic metal complex to the second reactant, the metal complex comprises at least two anchor groups of a first anchor group species, which serve for the covalent binding of the metal complex via the ligands to the polymer.

The second reactant comprises at least one anchor group of a second anchor group species, which is suitable for the binding of the second reactant to a first anchor group of the ligand of the metal complex. The binding of the metal complex to the polymer results from the reaction of the at least two anchor groups of the metal complex with one second anchor group each of a second reactant.

According to a second strategy of the covalent linking of the organic metal complex to the second reactant, a third reactant takes part as "spacer" molecule in the first reaction.

Thereby, the ligand of the metal complex comprises at least two anchor groups of a first anchor group species, which is suitable for the covalent integration of the metal complex via the ligand into the matrix via a second anchor group. The second reactant comprises an anchor group of a first anchor group species, which serves for the binding of the second reactant to a second anchor group, so that the metal complex cannot directly bind to the second reactant. For the formation of a covalent bond between the ligand of the metal complex and the second reactant a third reactant is added, which comprises two anchor groups of a second anchor group species, wherein each of these anchor groups of the third reactant can form a covalent bond with one first anchor group each (namely of the metal complex and of the second reactant). Thus, the binding of the metal complex into the multidimensional network takes place via the ligand by reaction of the anchor group of the ligand of the metal complex and by reaction of the anchor group of the second reactant with the same third reactant, so that a cross-linking of the metal complex results.

The third reactant ("spacer" molecule) can be, for example, an alkyl chain of a desired chain length that comprises at two molecule parts spaced apart from each other, e.g. at ends opposite to each other, one anchor group each, which mediates the binding to the metal complex or to the second reactant. Besides alkyl chains, aryl, heteroaryl, alkenyl, alkinyl, trialkylsilyl and triarylsilyl groups and substituted alkyl, aryl, heteroaryl and alkenyl groups, optionally with substituents such as halogens, lower alkyl groups and/or electron donating and withdrawing groups, as well as common charge transport units such as, for example, arylamines, carbazoles, benzimidazoles, oxadiazoles etc. are also possible. The substituents can also lead to annulated ring systems.

Preferably, the metal complex and the second reactant are soluble in a common organic solvent (in particular for the production of OLED components). Besides alcohols, common organic solvents include ethers, alkanes as well as halogenated aliphatic and aromatic hydrocarbons and alkylated aromatic hydrocarbons, especially toluene, chlorobenzene, dichlorobenzene, mesitylene, xylene and tetrahydrofuran. In a preferred embodiment of the invention, the formed multi-dimensional network with cross-linked organic metal complexes is insoluble, which in particular makes the formation of a structure of several overlapping layers of such a multi-dimensional network possible in a simple manner.

Figure 2:
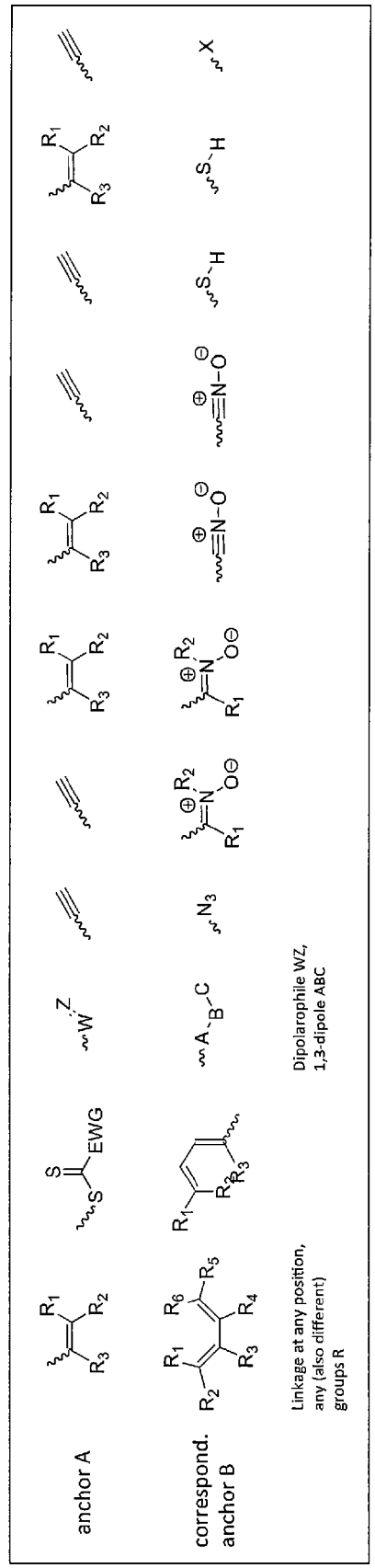
FIG. 2 shows selected examples of anchor groups of a first and a second anchor group species (each arranged in rows) in accordance with an embodiment of the present invention.

The first and the second anchor group may in particular be selected from the group of chemical groups shown in FIG. 2. If the metal complex is an emitter, the anchor group is preferably not conjugated to the emitter system in order not to affect the emission of the complex.

In principle, any organic transition metal complex, which carries at at least one of its organic ligands a first anchor group, can be used in the method. In particular, besides the first anchor group, the metal complex comprises at least one metal center and at least one ligand. The metal complex can be mononuclear or polynuclear (di-, tri-, tetranuclear, etc.) and can carry one or several ligands. The ligands can be mono- or polydentate. If a mononuclear complex carries only one ligand, this ligand is polydentate. If the complex is not neutral, a corresponding counter ion has to be provided, which preferably does not take part in the first reaction as described herein.

During the occurring reaction, the ligands at the metal center are not exchanged or replaced by other ligands. The occurring reaction takes place exclusively directly at the ligand or in the ligand sphere, the basic structure of the metal complex remains unchanged.

The occurring reaction constitutes a covalent linkage, wherein the resulting new covalent bonds are preferably formed between non-metal elements.

Preferred organic metal complexes are, for example, light emitters, which can be applied in optoelectronic components, such as OLEDS. Another group of preferred metal complexes are semiconductors. Such emitting and semiconducting metal complexes are known in the state of art.

The number of anchor groups at a metal complex is depending on whether the metal complex shall be bound in a single-sided or in an at least double-sided manner to a polymer.

For a single-sided binding of a metal complex to a polymer, the metal complex comprises one anchor group.

At least one ligand of the metal complex comprises a first anchor group. Taken together, for an at least double-sided binding, a metal complex comprises at least two anchor groups, preferably of one anchor group species, which can be arranged at one ligand or are preferably distributed to two ligands of the metal complex. Thus, it is also possible that several ligands of a metal complex comprise one or several anchor groups, wherein the number of anchor groups at the metal complex and at the second ligand determines the degree of cross-linking.

The multi-dimensional network formed in a preferred embodiment of the method by binding of a metal complex to more than one polymer (at least double-sided binding) is a two-dimensional or three-dimensional network. A three-dimensional network is preferred.

The second reactant used in the method can be selected from a group consisting of a monomer, a oligomer and a polymer. Low-molecular, reactive molecules are here referred to as monomers, which can react to molecular chains or networks, to unbranched or branched polymers. Examples are common monomers such as styrene, ethylene, propylene, vinylchloride, tetrafluoro ethylene, acrylic acid methylester, methacrylic acid methylester, bisphenol A/phosgene, ethylene glycols, terephthalic acids and organochloro silanes. A molecule which is composed of 2 to 30 structurally identical or similar units is referred to as oligomer herein. Examples of oligomers are oligoethylene, oligopropylene, oligovinylchloride, oligotetrafluoro ethylene, oligoacrylic acid methylester, oligomethacrylic acid methylester, oligocarbonates, oligoethylene glycol, oligoethylene terephthalate, oligo(organo)siloxanes. Polymers are molecules which are composed of at least 10, preferably at least 15, more preferably at least 20 and most preferably of at least 30 structural identical or similar units. Examples of polymers are polystyrene, polyethylene, polypropylene, polyvinylchloride, polytetrafluoro ethylene, polyacrylic acid methylester, polymethacrylic acid methylester, polycarbonates, polyethylene glycol, polyethylene terephthalate, and poly(organo)siloxanes.

To date, cross-linking is only known between polymers, which are bound to metal complexes, wherein the polymers always react in a cross-linking reaction to themselves, thus are only homo-cross-linked. In contrast, according to the invention, cross-linking is initiated by the formation of a bond at the ligands of the metal complex, whereby the corresponding polymers are hetero-cross-linked with the metal complex.

In other words, the invention relates in one embodiment to materials, in particular to liquid-processable optoelectronic materials, which ensure due to their special structure both the covalent binding of a metal complex, for example a highly efficient emitter metal complex, to a functionalized second reactant in the form of a polymer, and optionally their cross-linking which leads to insolubility.

In a preferred embodiment of the invention, a fourth reactant is used in the first reaction of the method besides the metal complex, the second reactant and optionally the third reactant, wherein the fourth reactant concerns a hole or electron conducting chemical group and/or a charge blocking chemical group, which can also be cross-linked as a charge transport unit or a charge blocking unit. Examples for hole or electron conducting chemical groups are arylamines such as N,N'-bis(naphthalene-1-yl)-N,N'-bis(phenyl)-benzidine, N,N'-bis(naphthalene-1-yl)-N,N'-bis(phenyl)-2,2'-dimethylbenzidine, carbazoles such as 4,4-bis(carbazole-9-yl) biphenyl, 1,3-bis(carbazole-9-yl)benzene, benzimidazoles such as 1,3,5-tris(1-phenyl-1H-benzo[d]imidazole-2-yl)benzene, oxadiazoles such as 2-(4-biphenyl)-5-(4-tert-butylphenyl)-1,3,4-oxadiazole, triazoles such as 3-(4-biphenyl)-4-phenyl-5-tert-butylphenyl-1,2,4- triazole, 4-(naphthalene-1-yl)-3,5-diphenyl-4H-1,2,4-triazole.

The fourth reactant also comprises at least one anchor group of the first and/or the second anchor group species for the connection to the polymer and/or the metal complex, depending whether the fourth reactant shall be bound to the metal complex or to the second reactant.

Energetically favored reactions, referred to in the art as "click chemistry", which proceed specifically and result in a single product (H. C. Kolb, M. G. Finn, K. B. Sharpless, *Angew. Chem. Int. Ed.* 2001, 40, 2004-2021), can be used particularly for the first reaction. Thus, the "click chemistry" comprises reactions, which are performable with high yields, are applicable in a broad range of applications, proceed (stereo)specifically, comprise simple reactions conditions (preferably insensitive to water and oxygen), comprise easily removable, as nonhazardous as possible side products and reagents (if at all), proceed in environmentally friendly and/or easily removable solvents such as water or without solvents and/or need a simple purification (extraction, phase separation, distillation or crystallization—preferably no chromatography) or no purification at all.

"Click" reactions are in most cases highly thermodynamically favored with often more than 20 kcal mol$^{-1}$, leading to a single product with fast conversions and high selectivity. In most cases, carbon heteroatom bonds are formed with click reactions.

According to the invention, in particular nucleophilic substitutions, especially ring opening of tense electrophilic heterocycles such as epoxides and aziridines, carbonyl chemistry of the "non-aldol" type such as the formation of aromatic heterocycles or hydrazones, additions to carbon-carbon double bonds such as the oxidative formation of epoxides and azriridines, dihydroxylation and Michael additions as well as cycloadditions to unsaturated C—C bonds, in particular 1,3-dipolar cycloadditions and Diels-Alder reactions can be applied. Further examples for such reactions are cross-coupling reactions for the formation of C—C bonds such as the Ullmann reaction, the Sonogashira reaction and the Glaser coupling. All of these reactions are known to the person skilled in the art.

In the context of the invention, particularly such reactions are preferred which do not need the addition of another reactant (i.e. a reactant other than the first, second and, if applicable, the third and, if applicable, the fourth reactant), i.e. reactions that need at the most a catalyst that does not interfere with any further use. Examples for such reactions are, besides the 1,3-bipolar cycloadditions and Diels-Alder reactions mentioned above, nitrone-alkyne reactions, nitril oxide-alkyne reactions, thiol-ene reactions, thiol-yne reactions, thiol-isocyanite reactions, tetrazole-alkene reactions and other methods known as click reactions in the chemical literature.

Figure 3:
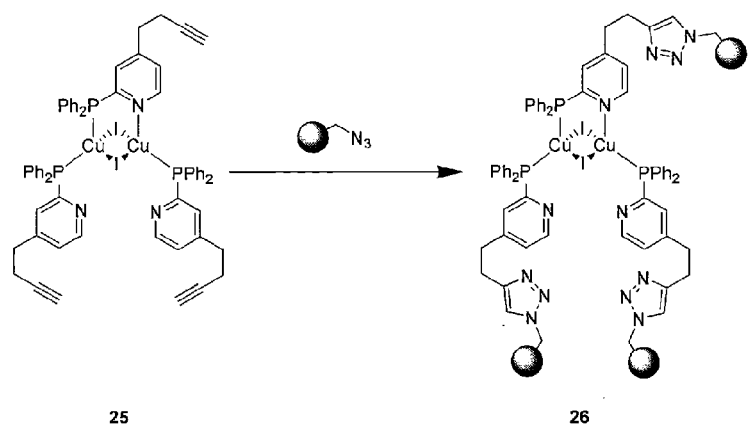
FIG. 3 shows a reaction for the cross-linking of an alkyne substituted copper complex with a polymeric azide as second reactant, wherein the reaction proceeds self-catalyzed in accordance with an embodiment of the present invention.

As described above, the first reaction takes place in the presence of a catalyst for the catalysis of the reaction. The catalyst is an educt/reactant and at the same time a catalyst. Thereby, the metal complex comprises the catalyst, i.e. the metal center contained in the organic metal complex serves also as a catalyst, so that a self-catalyzed binding of the metal complex to the polymer takes place. As an example, the copper-catalyzed click reaction between a terminal or activated alkyne as first anchor group of a first anchor group species of a metal complex and an azide as anchor group of a second anchor group species of a polymer is shown in FIG. 3.

For example, the classic 1,3-dipolar cycloaddition (Huisgen cyclisation), which otherwise needs rather high temperatures, proceeds non-regiospecifically and thus is generally not suited as "click" reaction (V. V. Rostovtsev, et al., *Angew. Chem. Int. Ed.* 2002, 41, 2596-2599; C. W. Tornøe, et al., *J. Org. Chem.* 2002, 67, 3057), proceeds using a Cu(I) catalyst compared to the classic cyclisation up to $10^7$ times faster, regioselective (only the 1,4-regioisomer is formed), also in water, at room temperature and is thereby insensitive to most other functional groups such as, for example, alcohols, acids and acid derivatives, carbonyl compounds, halogens etc.

In a preferred embodiment the metal complex is a Cu(I) or a Cu(II) complex, so that the reaction takes place self-catalytically. Other possible catalysts as part of a metal complex are Re, Fe, Ru, Os, Co, Rh, Ir, Ni, Pd, Pt, Ag, Au, Zn, Cd, Hg, Sn and/or Pb.

The reaction between metal complex and second reactant proceeds preferably at a temperature which is higher than room temperature. At least 50° C. are preferred, particularly preferred are temperatures from 80° C. to 120° C. The reaction time needed at the particular reaction temperature can be easily determined by a person skilled in the art. Usually, a reaction time of 1 minute to 60 minutes, preferably of 10 minutes to 30 minutes is to be anticipated, so that the metal complex is immobilized and thus stabilized and insoluble. The thermal activation can thereby also be carried out by exposure to microwaves, whereby the reaction times can be shortened considerably to less than 1 minute.

If an anchor group, for example an alkyne linker, is present in conjugation to an organic ligand of the metal complex and an aromatic azide is used as complementary anchor group, the emission colors of such emitting complexes, which are based on charge transfer transitions between the metal ions and the ligands, can be influenced. In this context, metal complexes with three or more ligands (e.g. four, five or six ligands) are preferred, since thereby three or more linking positions (e.g. four, five or six linking positions) are present. Thus, the complexes can thereby be linked to the polymers as well as connected to hole or electron conductors (fourth reactants). The optical, mechanical and electrical properties of the obtained substances can thus be influenced by the particular composition of the azide mixture.

If the method described herein leads to an insoluble product according to a preferred embodiment of the invention, it is possibly to easily arrange several stacked layers of immobilized metal complexes, without the need for using, for example, orthogonal solvents.

For the production of a multi-layer arrangement, a second reaction is performed after the first reaction described above. This second reaction comprises a fifth reactant in the form of an organic metal complex and a sixth reactant for the formation of a preferably insoluble multi-dimensional network, wherein the metal complex is cross-linked during the formation of a multi-dimensional network through covalent bonds. With regard to special embodiments of the second reaction, aspect described for the first reaction apply here analogously.

Thereby, the fifth reactant of the second reaction can be identical to or different from the first reactant of the first reaction. Likewise, the sixth reactant of the second reaction can be identical to or different from to the second reactant of the first reaction.

The cross-linking that occurs according to a preferred embodiment of the method of the invention allows for a fast and simple disposal of any number of photoactive layers, whose solubility does not have to be adjusted to each other as in previous systems. This results in a considerable simplification of the processing, since the selection of the individual active layers does no longer have to be orthogonal to each other with regard to solubility, but can be selected almost independently from each other. This allows for the sequential disposition of any number of different layers and thereby leads to a significant increase of efficiency and durability.

In a preferred embodiment of the method, the anchor groups of the first and the second anchor group species are present in equimolar amounts, so that all anchor groups can form covalent bonds with complementary anchor groups.

According to a second aspect, the invention relates to the use of a polymer obtained with the method described herein, in particular as an emitter or an absorber in an optoelectronic component.

In particular in cases in which the metal complex is an emitter metal complex, which can and shall be applied in optoelectronic components, an advantage of the invention is the stabilization of the geometry of the emitter metal complex by the immobilization through cross-linking.

It is known that a change of geometry of an emitter complex by excitation from the ground state to the first excited state leads to greater shifts of the energy potentials and to higher possibilities for non-radiative relaxation processes. Therefore, the geometry of the excited state should not differ from that of the ground state. Thus, the spatial/sterical stabilization of emitters achieved by use of the invention leads to an increase in efficiency of emitters as metal complexes.

Due to the anchor groups for the linking click-reactions that are present in the periphery of the ligands of metal complexes, e.g. as emitter complexes, the possible movement of the ligands of the metal complexes to each other is limited. Thus, the complexes are fixed and stabilized. The transition probabilities for non-radiative processes are reduced by rotation and twisting in contrast to "free" complexes: The emission quantum yields of the emitters are increased. Simultaneously, the fixation leads to maximal utilization of the energetic gap between the ground state and the first excited state. Hereby, in comparison to the "free", i.e. not cross-linked complex, a blue shift of the emission spectrum can take place, because the population of rotational and vibrational states is less probable and the energy difference between the ground state and the first excited state (direct vertical alignment of the potential curves, cf. Franck-Condon-principle) is maximized. It is possible to shift the emission of a given free, i.e. not cross-linked, emitting metal complex in the direction of or into the blue spectral range by means of immobilization.

In addition to the layer stabilization and the possible integration of defined hole and electron conductors, the invention also improves the efficiency of optoelectronic components: Due to the sterical hindrance of the metal complexes the overlapping integrals between states not used for emission decrease, the population of rotational and vibrational states become less likely. The stability of the complexes increases due to the prevention of bond breaking and non-radiative relaxations through free mobility of the ligands of a metal emitter system. By means of the immobilization it is possible to shift the emission of a given free, i.e. not cross-linked, emitting metal complex in the direction to or into the blue spectral range.

According to a third aspect, the invention relates to the use of a polymer, produced according to the method described herein, with a covalently bond metal complex as an emitter or an absorber in an optoelectronic component, provided that the metal complex is a light emitter or a light absorber.

Accordingly, in a fourth aspect the invention relates to an optoelectronic component comprising an organic metal complex covalently bound to a polymer, as described herein.

The optoelectronic component can be an organic light-emitting diode (OLEDs), a light-emitting electrochemical cell (LEECs or LECs), OLED sensors, optical temperature sensors, organic solar cells (OSCs), organic field effect transistors, organic diodes, organic photodiodes and "down conversion" systems. Such components are known to a person of skill in the art.

According to a fifth aspect, the invention relates to a method for the production of a layer of an organic metal complex bound to a polymer, in particular to a thin layer with a thickness of 75 nm to 300 nm, in particular 100 nm to 250 nm, particularly for the production of an optoelectronic component.

The method depends on whether the metal complex is bound single-sided or at least double-sided to the polymer. In the first case, liquid-processing is performed with the reaction product, because the solubility of the metal complex is increased by the binding to the polymer. In the second case, the of the mixture of both reactants can be applied onto a solid support by all methods known in the state of art, in particular by inkjet printing, dipping, spincoating, slot-die coating or knife coating. The reaction product is insoluble.

In the first case the further liquid-processing of the thus obtained composite material can be carried out by means of all coating and printing methods known in the state of the art, in particular by means of inkjet printing, dipping, spincoating, slot-die coating or knife coating (knife coating).

In the second case the method comprises at least the following steps: First, a mixture of a first reactant in the form of an organic metal complex and a second reactant in the form of a polymer in solution is prepared. Common organic solvents used include besides alcohols also ethers, alkanes as well as halogenated aliphatic and aromatic hydrocarbons and alkylated aromatic hydrocarbons, in particular toluene, chlorobenzene, dichlorobenzene, mesitylene, xylene, tetrahydrofuran, phenetole and/or propiophenone.

During the first reaction, the metal complex is bound single-sided to the polymer and, in a preferred embodiment as described above, is bond in a multi-sided fashion (cross-linked), wherein the reaction between the first reactant and the second reactant is catalyzed by the metal complex.

As described herein, the formation of the single-sided or at least multi-sided connection is carried out at higher temperature, preferably between 80° C. to 120° C.

According to a sixth aspect, the invention relates to the use of a metal complex bound to a polymer as an emitter material for an optoelectronic component, in particular as optoelectronic ink.

In a seventh aspect, the invention relates to an organic metal complex with at least one metal center and at least one organic ligand. According to the invention, the metal complex comprises one, preferably two, three, four or more anchor groups of a first anchor group species for the reaction with an anchor group of a second anchor group species for the single-sided or multi-sided connection, wherein the anchor group of the metal complex can form a covalent bond with the anchor group of a second reactant during the first reaction.

According to an eighth aspect, the invention relates to the use of such a metal complex for the connection and optionally cross-linking and thus immobilization of the metal complex to a second reactant, in particular in the form of a polymer, which comprises an anchor group of a second anchor group species. At the same time, the invention relates to the use of a polymer for increasing the solubility of a metal complex by the single-sided connection described herein.

In a ninth aspect, the invention relates to a method for the functionalization of an organic metal complex with one, two or more anchor groups through which the metal complex is bound to a second reactant carrying a second anchor group and can optionally (in case of at least double-sided binding) be immobilized, since the anchor group(s) of a first anchor group species of the metal complex (each) react with the anchor group of a second anchor group species of the second reactant to form a covalent bond.

In FIG. 2, the anchor groups shown opposite to each other can, bound on the one hand to the metal complex and on the other hand to the second reactant, form a covalent bond between the reactants and thus link and, if applicable, immobilize the metal complex. First and second anchor group species are addressed here as anchor A and anchor B. Depending on the use, the anchor A shown here can represent the first or the second anchor group species and the anchor B can represent the second or the first anchor group species, respectively.

The meaning of the symbols used is as follows:

R1-R6 can each independently be hydrogen, halogen or substituents, which are bound via oxygen (—OR*), nitrogen (—NR*2) or silicon atoms (—SiR*3) as well as alkyl (also branched or cyclic), aryl, heteroaryl, alkenyl, akinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carbonyls, carboxylates and their esters, and CF3 groups. R1-R6 can optionally also lead to annulated ring systems;

R*=organic group, selected from the group consisting of: hydrogen, halogen or deuterium, as well as alkyl (also branched or cyclic), aryl, heteroaryl, alkenyl, akinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carboxylates and their esters, and CF3 groups;

X=halogen, OSO2Me, OSO2Tolyl, OSO2CF3.

In FIG. 3, the ball shown stands for polystyrene as an example for a second reactant.

Figure 4:
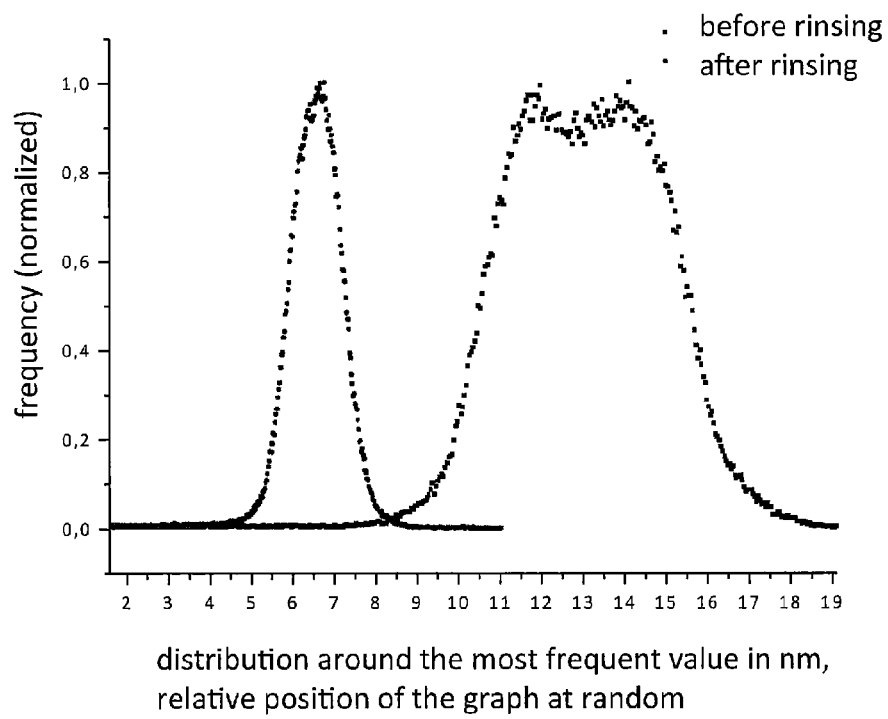
FIG. 4 shows a histogram of the AFM-picture before and after rinsing with xylene (see example 3) in accordance with an embodiment of the present invention.

In FIG. 4, the heights are normalized to 1, the position of the histograms on the X-axis is arbitrary, but true to scale. For a better overview, the histograms were not arranged on top of each other, but side by side. The processing was carried out at 40° C., the scan-size of the underlying images is 1 μm2.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

EXAMPLES

The invention is a stabilization, connection and optionally cross-linking method of metal complexes with polymers, which consist of one or more metals and one at least bidentate, or several mono- or polydentate ligands. According to the invention, the organic metal complex and the second reactant carry complementary chemical anchors of a (first or second) anchor group species, which are covalently bound to each other in a reaction proceeding as quickly and completely. Therefore, for example, luminescent or semiconducting metal complexes can be immobilized, e.g for applications in organic electronics, in order to increase the lifetime and long-term stability of the components.

Example 1

In the invention such reactions are preferred which do not need the addition of another reactant besides the metal complex and the second reactant, i.e. reactions that need at the most a catalyst that does not interfere with the further use. Examples for such reactions are 1,3-bipolar cycloadditions, Diels-Alder reactions, nitrone-alkyne reactions, nitril oxide-alkyne reactions, thiol-ene reactions, thiol-yne reactions, thiol-isocyanite reactions, tetrazole-alkene reactions and other methods known as click reactions in chemical literature.

These are reactions, which are catalyzed by the metal itself contained in the metal complex, on other words a self-catalyzed connection or cross-linking. One example is the copper-catalyzed click reaction between a terminal or activated alkyne and an azide. This reaction provides regioselectively and in high yields and conversions 1,4-triazoles (see FIG. 2).

Example 1.1

Cu Complex Catalyzed Click Reaction Between Terminal Alkynes and Azides

Phenylacetylene (103 mg, 1.0 mmol, 1.0 eq.) and benzyl azide (133 mg, 1.0 mmol, 1.0 eq.) were dissolved in an air-tight lockable vial with a septum in 10 mL dry dichloromethane. The Cu complex (catalytic or stoichiometric amounts) was added, the vial sealed and the reaction stirred at room temperature for 2 days. For the removal of the catalyst complex the reaction mixture was put in 50 mL methanol and stirred for 20 min. The complex was removed by filtering and the filtrate was concentrated. Removal of the solvent and drying of the product in high vacuum resulted in the compound 1-benzyl-4-phenyl-1H-1,2,3-triazole as light yellow solid with 95% yield (245 mg, 0.95 mmol). The identity of the product was proven by NMR-spectroscopy, infrared spectroscopy and high-resolution mass spectroscopy.

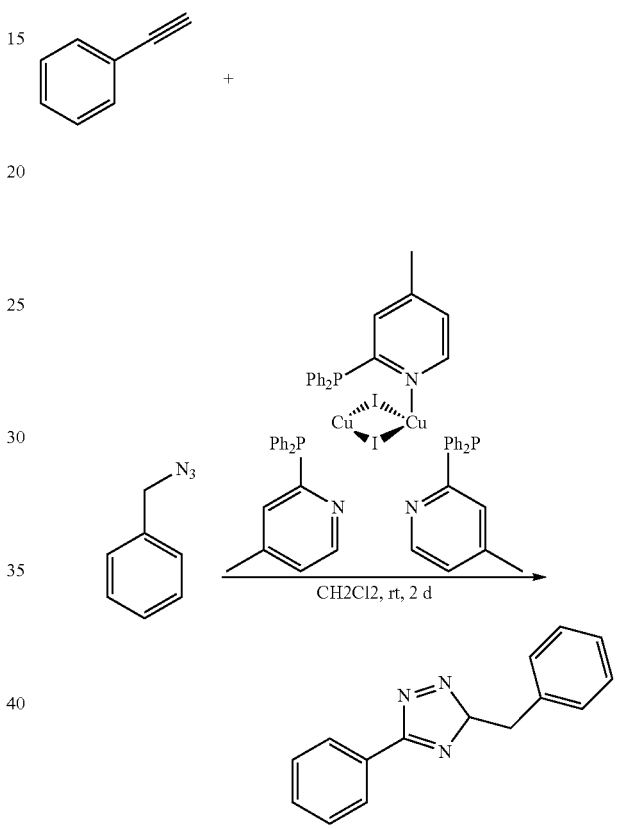

Example 1.2

Cu-Complex Catalyzed Click Reaction Between Cu Alkyne Complex and Azides

The Cu complex (1,341 g, 1.0 mmol, 1.0 eq.) was dissolved in an air-tight lockable vial with a septum in 10 mL dry dichloromethane and benzyl azide (466 mg, 3.5 mmol, 3.5 eq.) was added. The reaction was stirred at room temperature for 12 hours, filtered over a syringe filter and precipitated by adding dropwise into diethyl ether. Rinsing of the precipitated solid with diethyl ether and drying of the product in high vacuum resulted in the compound tris-(4-(2-(1-benzyl-1H-1,2,3-triazol-4-yl)ethyl)-2-(diphenylphosphino)pyridin)-di-copper-diiodide as light green solid in 61% yield (1.052 g, 0.61 mmol). The identity of the product was proven by NMR-spectroscopy, infrared spectroscopy mass spectroscopy and elemental analysis.

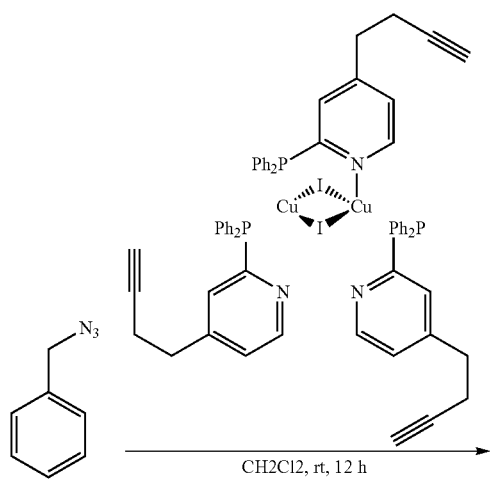

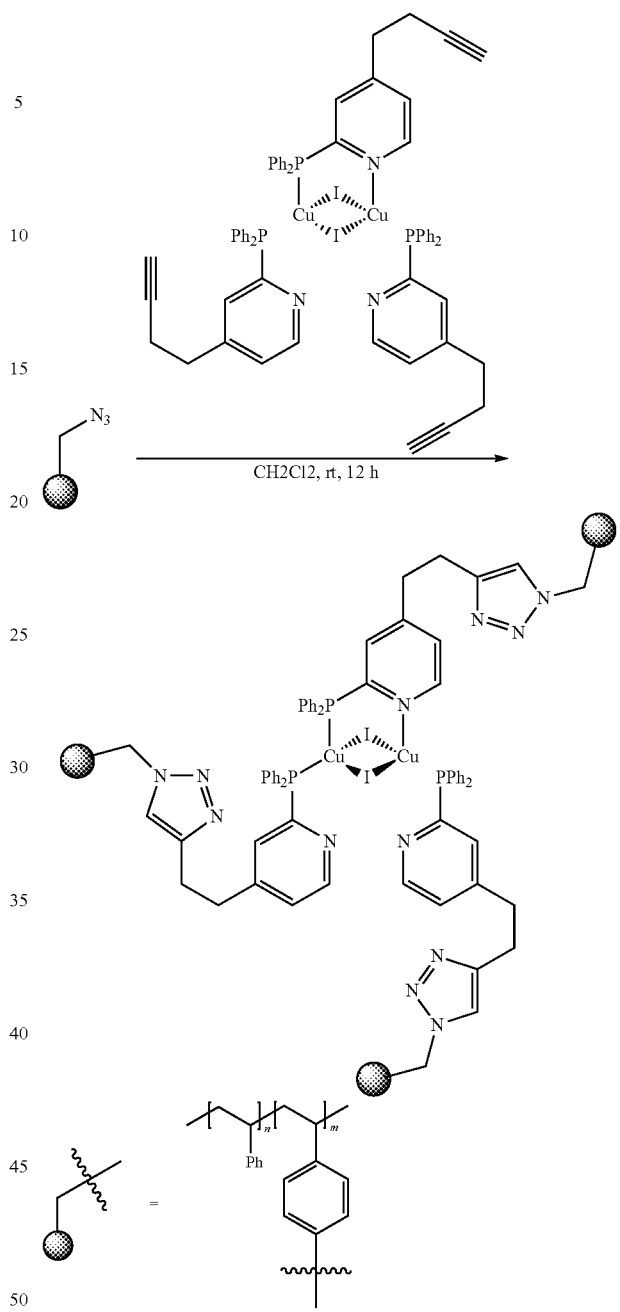

Example 1.3

Cu Complex Catalyzed Click Reaction Between Cu Alkyne Complex and Polyazides for Cross-Linking The Cu complex (440 mg, 0.33 mmol, 1.0 eq.) was dissolved as first reactant in an air-tight lockable vial with a septum in 10 mL dry dichloromethane and converted with poly-(vinylbenzylazide-alt-styrene) (370 mg, 1.0 mmol, 3.0 eq.). The reaction was stirred at room temperature for 12 hours, whereat the product precipitated as insoluble greenish solid from the reaction solution. The precipitate was withdrawn by suction, washed with 20 mL dichloromethane, 20 mL diethyl ether and 20 mL methanol and dried in high vacuum. The product poly-(4-(2-(1-(4-vinylbenzyl-1H-1,2,3-triazole-4-yl)ethyl)-2-(diphenylphosphino)pyridine)-alt-styrol@ CuI was a light green solid in 66% yield (540 mg, 0.21 mmol) and represents a cross-linked metal complex. The identity of the product was clearly proven by infrared spectroscopy and elemental analysis.

It was shown that such a reaction provides insoluble, cross-linked metal complexes (composite materials). Starting complex 25 as well as product 26 (see FIG. 2) show a yellow luminescence, whose spectrum is not further influenced or disturbed by the reaction since the anchor groups are not in conjugation to the emitter system.

After application onto a glass slide using a knife-coating apparatus (all other known printing or coating methods such as, for example, spin-coating, slot-die or ink-jet are also possible) in a thin layer and curing by heating to 100° C. for 30 minutes, this layer became stabilized and insoluble. Using this method, multilayer arrangements, which otherwise need orthogonal solvents or photochemical curing steps for implementation, can be easily realized. In addition, this cross-linking provides for a stabilization and fixation of the geometric structure of the metal complexes, preventing a movement of the ligands and thus a change in structure of the excited molecules and effectively inhibiting a reduction in efficiency due to non-radiative relaxation pathways.

Example 2

The invention relates in a preferred embodiment to the production of novel optoelectronic inks as emitter materials for organic light-emitting diodes as optoelectronic component. In one embodiment, the ink is based on electroluminescent copper(I) complexes, in which diphenylphosphinepyridines, diphenylphosphinechinolines and related heterocycles are used as ligands. These bidentate ligands form polynuclear complexes with copper(I) iodide with a ligand to metal iodide ratio of 3:2.

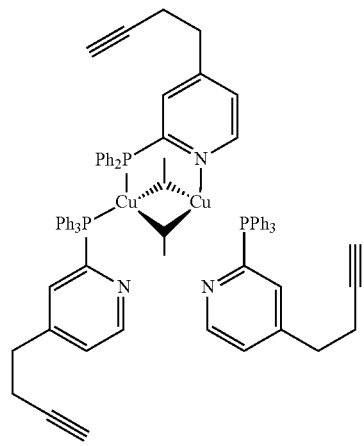

Structure of tris-(4-butinyl-2-diphenylphosphinopyridine)-bis-(copper iodide)

As shown in experiments, these ligand systems can be substituted with alkyne chains such as 4-butyne and coupled as a copper complex (first reactant with first anchor group) in a click reaction with azides. With this reaction, low-molecular as well as polymeric azides can be converted as a second reactant so that, for example, cross-linked, copper-containing polymers can be synthesized, which combine the electroluminescent properties of the metal complexes with the advantages of the simple liquid processing of the polymers and result in robust, insoluble layers after one baking step. In the case of a single-sided connection, the advantages of liquid processing of the resulting soluble metal complex polymer composite materials (short composite materials) can be used; in the case of multilateral connection, cross-linked insoluble layers for the realization of multi-layer arrangements result.

Furthermore, this reaction can be carried out with other ligand classes. At the same time, further material functions can be implemented into the ink in addition to the connection or cross-linking. Therefore, click-reactions can be used in order to link functional semiconductors (as third reactant), which have hole-transporting or electron-transporting properties, to the complexes. If the anchor group, e.g. the alkyne linker, is linked in conjugation to the organic ligands and aromatic azides are used, the emission color of the complexes, which is based on charge-transfer transitions between the metal ions and the ligands, can be influenced. Since the dimeric complexes each contain three ligands and thus three positions for connection, the complexes can in this way be bound to the polymers as well as bound to hole and electron conductors. The optical, mechanical and electrical properties of the substances obtained that way can for this reason be influenced via the respective composition of the azide mixture. These parameters of the ink can be optimized by robot-supported high-throughput screening methods. With the use of different metal complexes substituted with alkynes, organic light emitting diodes in different colors can be realized, and white-light OLEDS can be achieved by suitable mixture of colors of the corresponding metal complexes.

Emitters (in particular emitters, which were synthesized via a fourth reactant for the transport or the blocking of electrical charges, which comprises an anchor group of the first or the second anchor group species) can be linked with an ideal mixture of hole conductors, electron conductors, and a polymer to an optoelectronic ink.

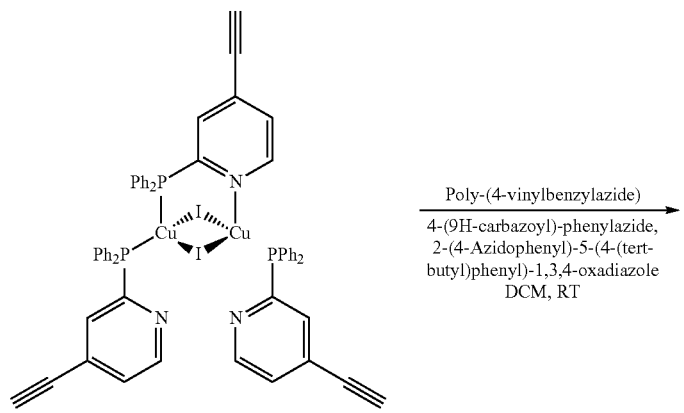

-continued

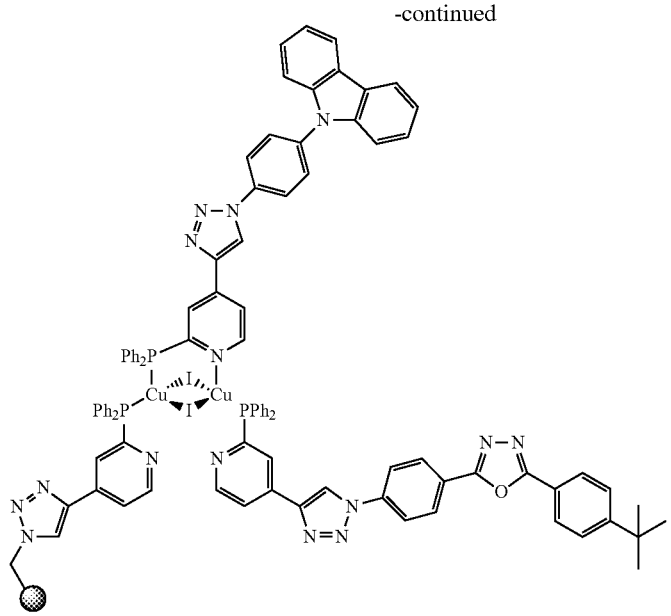

27

The ball shown in 27 stands for polystyrene, but can also represent any other polymer as second reactant.

In the process, the PyrPHOS complex (pyridyldiphenylphosphine=PyrPHOS) itself serves as a catalyst for the click reaction. By using polymeric azides with a polystyrene or polyethylene glycol backbone a single-sided connection is formed by reaction via only one anchor group of the metal complex.

As could be shown by photoluminescence spectroscopy, the yellow emission color of the copper-PyrPHOS complexes is influenced neither by variation of the charge transport or blocking units nor by the connection to the polymers. The emission maximum of the PyrPHOS-systems lies at 550 nm. By mixing the composite material with the hole conductor CBP in a single layer assembly, it was shown that the emission color observed by photoluminescence can also be reproduced in an OLED.

Example 3

Knife Coating Application

With the knife coating method, thin layers can be produced by means of a wedge-shaped coating knife. For this purpose, the substance is applied in solution onto a substrate and evenly distributed by means of a slide, which can be controlled with a definite gap width and drawing speed. The films thus produced are dried by heating and a nitrogen flow, so that extremely smooth, defined layers can be produced.

For the production of the thin layers, the polymer dissolved in xylene was mixed in a vial with the metal complex solved in dichloromethane and shortly after mixing was applied as a light cloudy solution to a substrate coated with indium tin oxide (ITO) and PEDOT:PSS. An equimolar stoichiometry was chosen.

The reaction, coating and drying were carried out at various temperatures. Since the whole process was finished after a very short period of time, the samples were subsequently tempered on a heating plate at 100° C. for one hour in order to reach a high yield of the Huisgen reaction. The samples were examined under a UV-lamp as well as by atomic force microscopy. Furthermore, the films were rinsed by immersion in xylene before and after drying for monitoring the reaction. While the cross-linked product is insoluble, the reactants dissolve in this solvent, so that by the resistance of the layers a conclusion about a successful cross-linking can be drawn.

With increasing process temperature the resistance to rinsing increased. After the tempering step, all tested layers were resistant to xylene. The different samples were measured by AFM (atomic force microscopy) in order to examine the morphology of the layers on a nano-scale level.

The impression gained by optical comparison that the properties of the cross-linked samples could not be changed by rinsing was confirmed by atomic force microscopy. In addition, the roughness $R_q$ (standard deviation of the height distribution curve) was determined (according to E. P. Degarmo, J. T. Black, R. A. Kohser, Materials and Processes in Manufacturing, 2003, 9. edition, Wiley, 223). For this, the whole scan area or a section of it in case of impurities were selected. The results are listed in table 1 below.

The roughness is very low for the measured samples with values between 0.53 and 1.64 nm, indicating an excellent morphology of the measured samples.

TABLE 1

Roughness of the AFM-samples. Pinholes appeared in the first four samples, the determination was therefore not carried out over the whole measuring range but over a hole-free area in order to obtain representative results.

| sample | | roughness $R_q$ | in relation to an area of |
|---|---|---|---|
| 80 | 11° C. | 0.66 nm | 0.478 µm² |
| 80 | 11° C. rinsed | 0.99 nm | 0.397 µm² |
| 81 | 25° C. | 0.53 nm | 0.485 µm² |
| 81 | 25° C. rinsed | 0.70 nm | 0.495 µm² |
| 82 | 40° C. | 1.64 nm | 1.000 µm² |
| 82 | 40° C. rinsed | 0.91 nm | 1.000 µm² |

Histograms are shown in FIG. 4 for comparison. Thus, quite sharp, almost Gaussian height distributions resulted. The standard deviation of these distribution curves is specified as $R_q$ in the table.

Example 4

Simultaneous Single-Sided Linkage of the Metal Complex

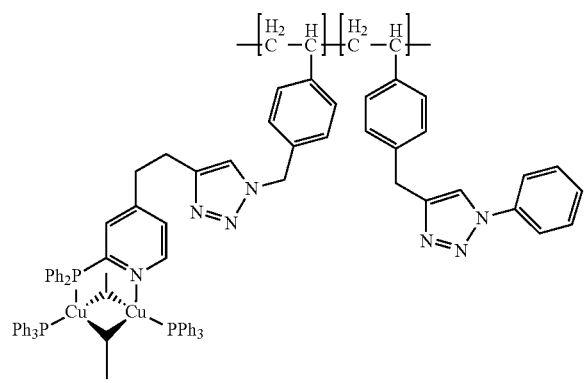

In order to bring copper complexes (first reactant) as emitter as well as charge transport units (third reactant) into a polymer (second reactant) in a simple modular manner, the metal complex, an excess of azide and penylacetylene were reacted. Both alkynes were linked to the polymer. Furthermore, the product luminesced as expected, thus the complex remained intact.

Example 5

Cu(I)-Catalysis with the PyrPHOS Complexes

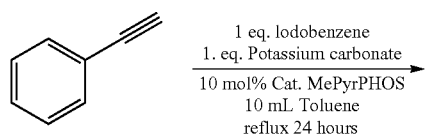

On the one hand, the catalytic potential of the PyrPHOS systems was to be evaluated beyond the Cu(I)-Huisgen reaction. The insoluble, cross-linked PyrPHOS polymers could represent a solid-phase catalyst with immobilized Cu(I).

On the other hand, the properties of the metal complexes can be modified with such reactions, e.g.:

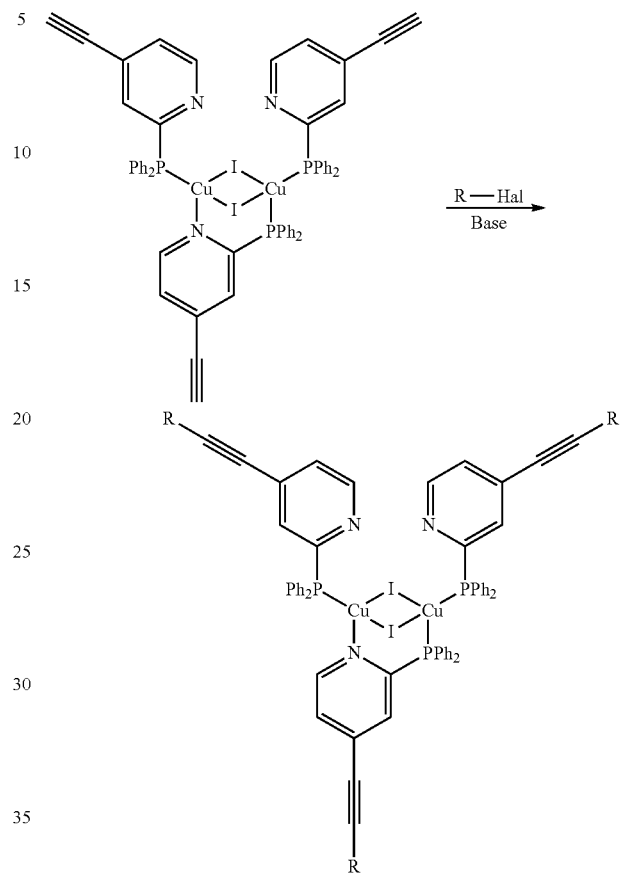

The reaction shown above proceeded with complete conversion (determined with IGC-MS). Furthermore, the catalyst that is insoluble in toluene could be filtered out together with the potassium carbonate and remained intact (preservation of the yellow photoluminescence).

Example 6

Thiol-Ene-Reaction

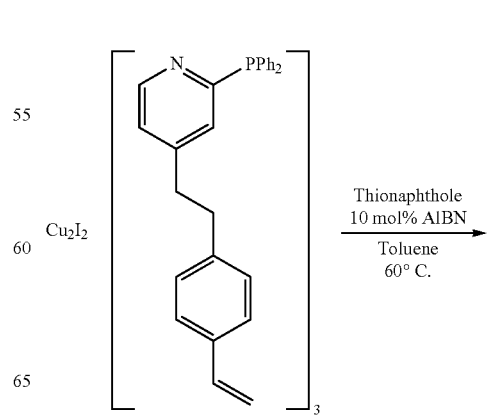

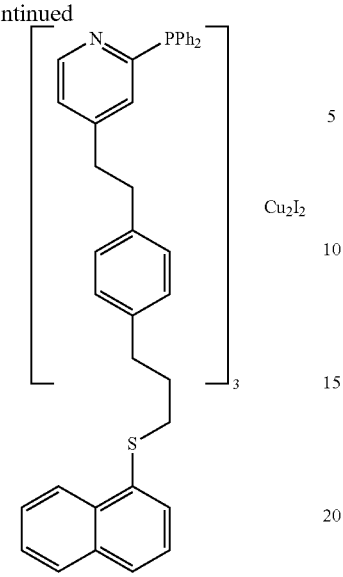

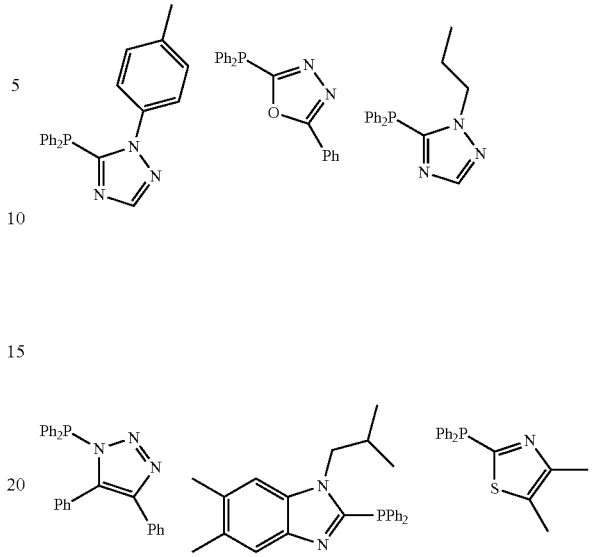

The product shown on the right side luminesced like the reactant shown on the left. The typical odor of a free thiol was lacking after the reaction.

Example 7

Reaction of Heteroleptic Complexes with Charge Transporting Groups

As described herein, charge transport units, as used, for example, for organic light emitting diodes can be incorporated by the linking reaction.

Dinuclear N^P-CuI complexes, which reacted with N-(4-azidpphenyl)-carbazole:

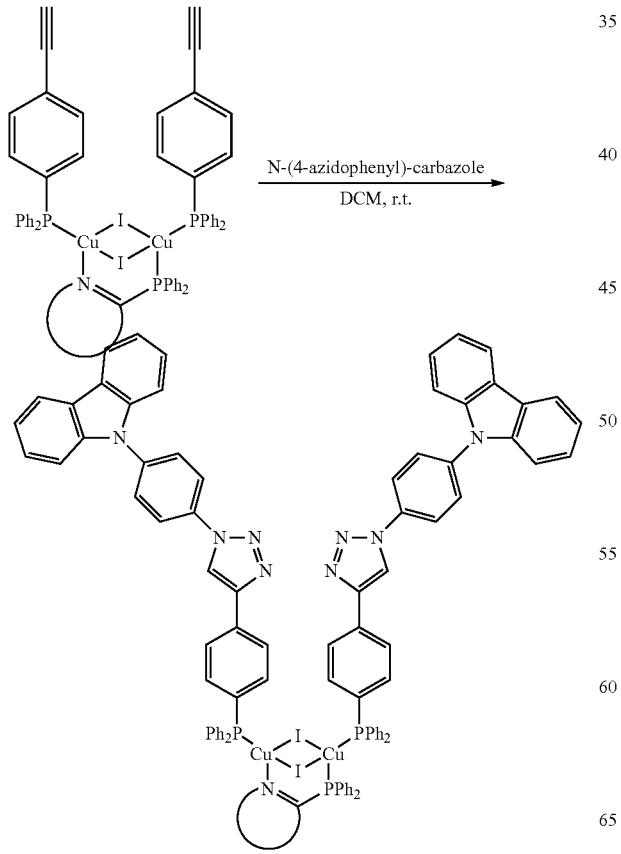

N^P-Ligands:

Example 8

Ligands for the Synthesis of Copper Complexes which Enable an Attachment by Huisgen Click Reaction Example 8.1

Synthetic Route to Alkyne-Modified Bisdiphenylphosphino Benzene Derivatives

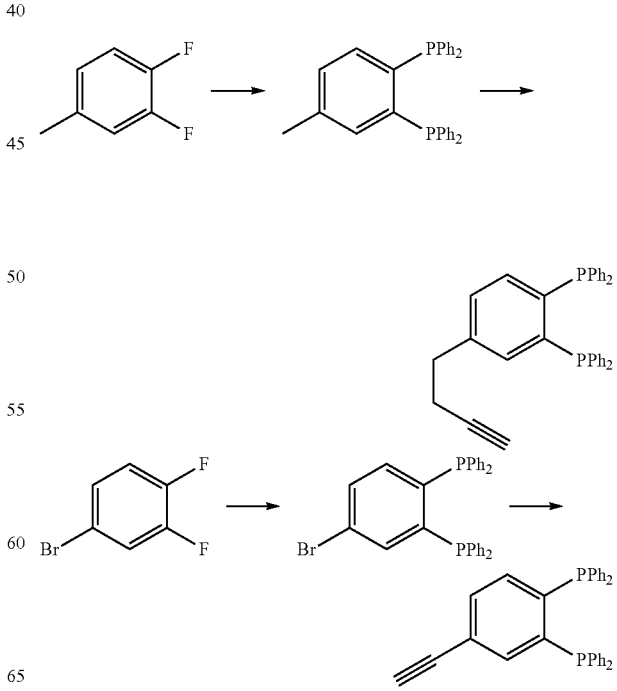

Example 8.2

Different Alkyne-Substituted Ligands which are Suitable for the Preparation of Alkyne-Substituted Copper Complexes

Example 9

Modification of Known Complexes for Achieving Linkage

By means of the invention, already known emitter complexes can be modified in order to realize a possibility for linking them. For this purpose, two or more suitable anchor groups are introduced into a complex. For this, all pairs of anchor groups shown in FIG. 2 are suitable.

Non-modified structure without anchor groups.

Modified structure with at least one anchor group.

Anchor group R

Ligand A

Ligand B

The basic structure in this figure is already known (Inorg. Chem. 2011, 50, 8293). By substitution with one or more anchor groups, a new structure is formed, which is cross-linkable or linkable. All anchor groups R can be attached to one of the ligands A or B or the anchor groups can also be distributed to both ligands. The cross-linking can be influenced by the number of anchor groups per complex.

Example 9.1

Modification of Known Structures

Known complexes can be modified by including anchor groups in a way that cross-linking is possible. Heteroleptic and homoleptic complexes can be used.

Modifiable, already known structures are listed in the figure. The ligands, which are suitable for a modification according to the invention, are highlighted in boxes. Some ligands such as halides and pseudo-halides are not suitable for such a modification due to chemical reasons. In charged complexes, such as the example from E. J. Org. Chem. in the figure, the luminescent ion, in this case the cation, should be linked.

*Inorg. Chem.* 2011, 50, 8293.

*J. Am. Chem. Soc.* 2011, 133, 12085.

*J. Am. Chem. Soc.* 2011, 133, 3700.

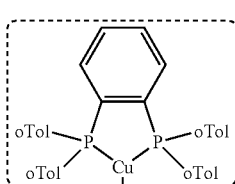

JACS 2011, 133, 10348.

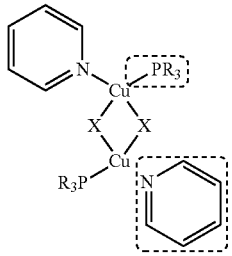

Aust. J. Chem. 1989, 42, 913.

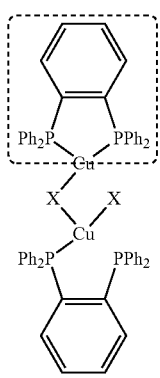

Inorg. Chem. 2007, 46, 1992.

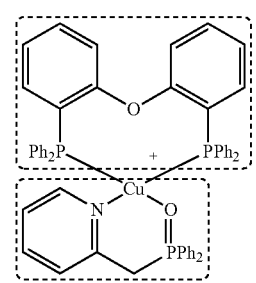

E. J. Org. Chem., 2010, 4009.

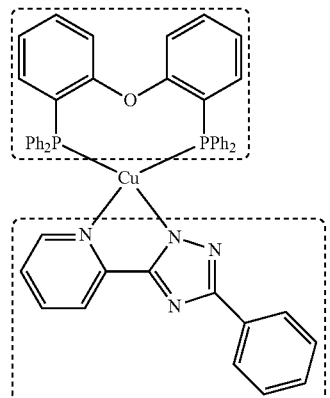

US20100252820_DeCola/BASF

Example 9.2

Synthesis and Spectroscopic Properties of Some Cross-Linkable Cu Complexes

In the following figures, three examples are shown that are suitable for linking to a polymer.

Synthesis of the Complexes 9.2 A and 9.2 B

Copper tetrakisacetonitrile tetrafluoroborate (1 mmol, 1 eq.) was provided with the corresponding neocuproine derivatives (1 mmol, 1 eq.) and the phosphines (1 mmol, 1 eq. for 9.2 A and 2 mmol, 2 eq for 9.2 B) in a small glass with stirring bar and septum under nitrogen and solved in 10 mL dry dichloromethane. The reaction mixture was stirred overnight, the volume reduced to the half in vacuum and the target compound precipitated by adding dropwise to n-hexane. The identity of the compound was proven by 1H-NMR, 31-P-NMR, elemental analysis and mass spectroscopy.

Complex 9.2 A

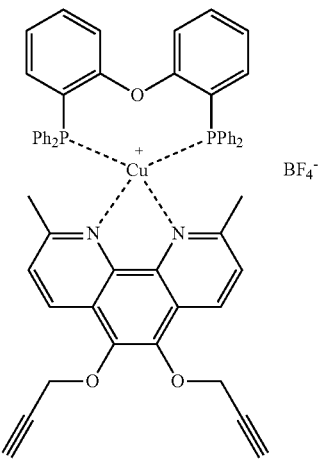

Complex 9.2 B

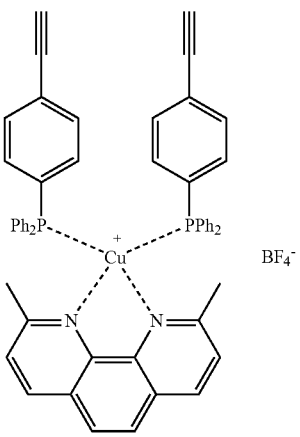

Complex 9.2 C

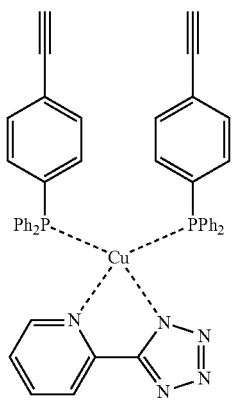

Figure 5:
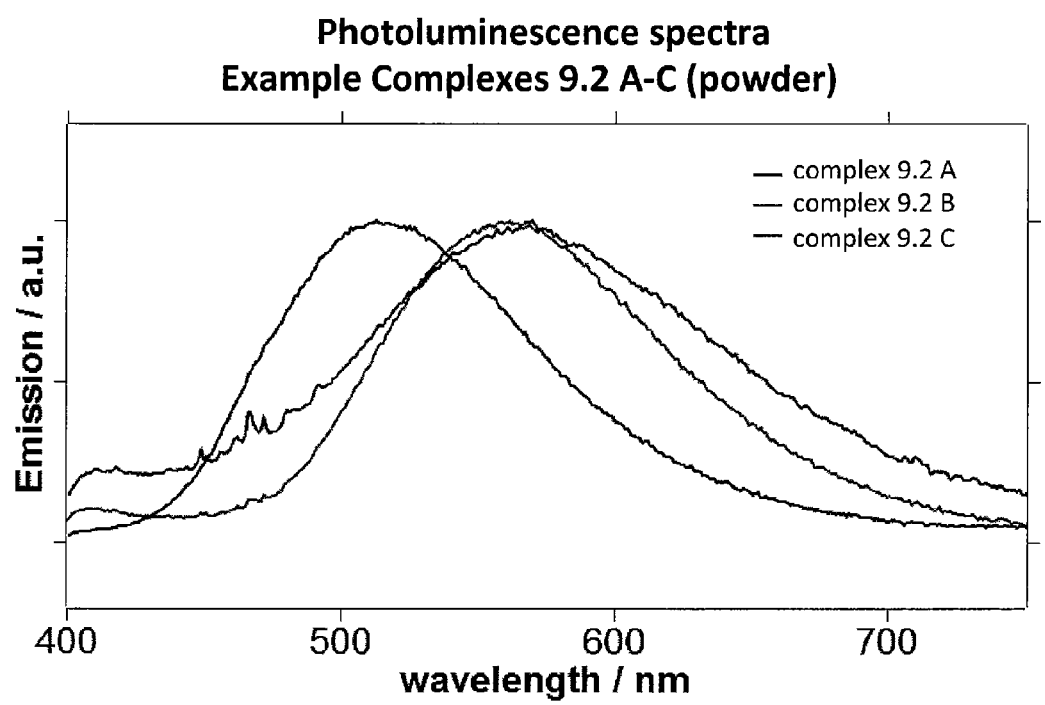
FIG. 5 shows the photoluminescence spectra of the compounds 9.2 A-C (powder measurement, room temperature, under normal atmosphere) in accordance with an embodiment of the present invention.

Photoluminescence spectra of the compounds were recorded (powder measurement, room temperature, under normal atmosphere): see FIG. 5.

Example 10

Assembly of the Anchor Groups

If one anchor group is used, a soluble composite material will result. If two anchor groups are used, which are spaced sufficiently far apart, a cross-linked, insoluble polymer composite is obtained.

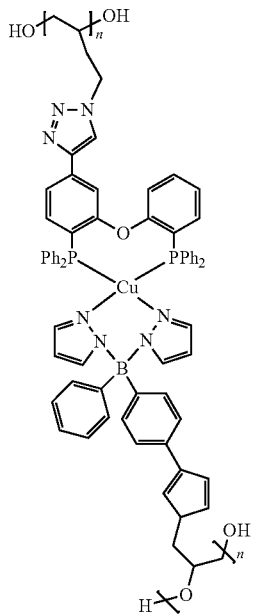

Insoluble, because of linkage to one string

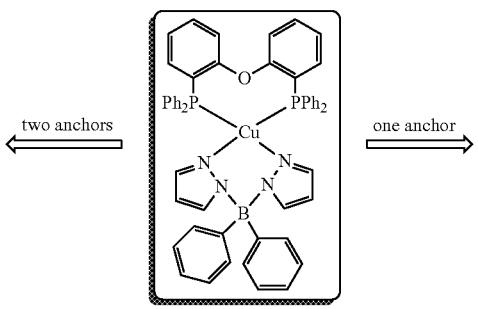

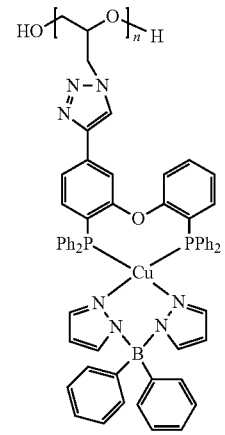

Soluble, because of linkage to one string

Important for the switching between linking and cross-linking is in this context also the positioning of the anchor groups: if two anchor groups are attached very close to each other on the same side of a molecule, the complex will not be effective as cross-linker, since preferably linkage to one polymer string takes place for geometric reasons.

This was seen for example complex 10 A:

Click Connection of Example 10 A

Complex 10 A (1 eq., 0.1 mmol) was solved in a 10 mL vial under nitrogen in dichloromethane. Glycidyl-azide-polymer "GAP" (2 monomer equivalents, 0.2 mmol) was solved in 0.5 mL dichloromethane and added to the complex solution. The reaction mixture was stirred over night, reduced to ⅓ of the former volume and precipitated by adding dropwise to hexane.

The identity of the example click complex 10 A-GAP was proven by 1H-NMR, infrared spectroscopy and elemental analysis.

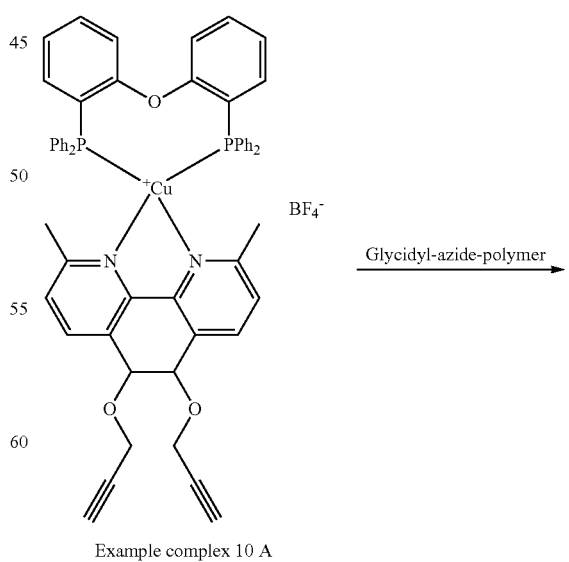

Example complex 10 A

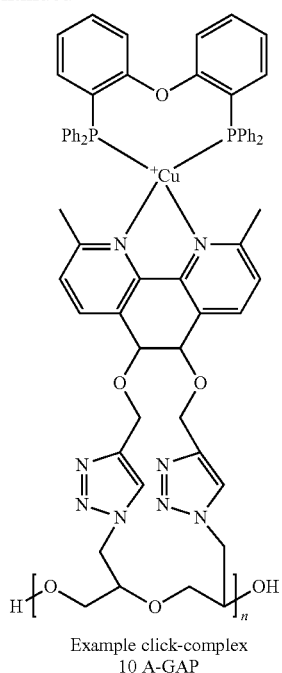

Example click-complex
10 A-GAP

All metal complexes listed in the following figure result in soluble composite materials, which were linked only via one side of the metal complex, when reacted with the glycidyl azide polymer functionalized with anchor groups.

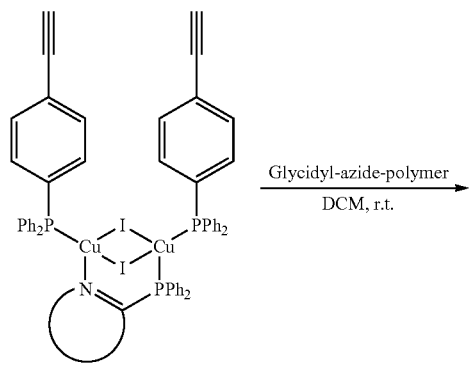

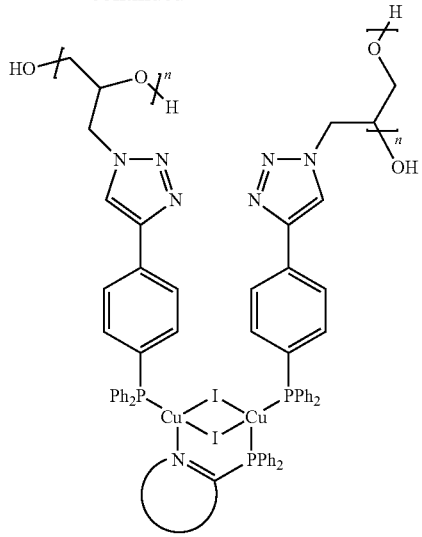

N^P-Ligands:

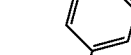
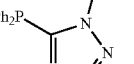
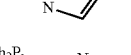
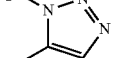

Example 11

Linking of Complexes which have Only One Anchor Group

If specific complexes are applied which possess only one single anchor group, potentially soluble complex containing polymers will be obtained. These are not cross-linked, but due to the polymeric backbone, have a strongly reduced diffusion tendency and facilitate that way the immobilization of metal complexes, for instance for catalysis or for optoelectronic applications in OLEDs.

Synthesis of the Complexes 11 A and 11 B

Copper tetrakisacetonitrile tetrafluoroborate (example complex 11 A 1 mmol, 1 eq.) and accordingly copper tetrakisacetonitrile hexafluorophosphate (example complex 11 B, 1 mmol, 1 eq.) was provided with the bisphosphine ligands POP (1 eq., 1 mmol) and the ligand 4-but-4'-in-2-diphenylphosphinoxido-pyridine functionalized with anchor groups (1 eq, 1 mmol) in a small glass with stirring bar and septum under nitrogen. 10 mL dry dichloromethane were added and the reaction mixture stirred at room temperature for 2 hours. The volume was reduced to the half in vacuum and the target compound precipitated by adding dropwise to n-hexane. The identity of the compound was proven by 1H-NMR, 31-P-NMR, elemental analysis and infrared spectroscopy.

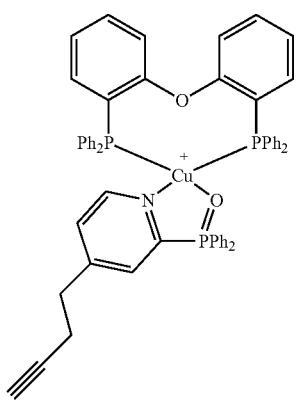

Example complex 11 A  BF$_4^-$
Example complex 11 B  PF$_6^-$

Example 12

Application of the Concept to Other Metal Complexes

This concept can also be applied to metals other than copper. Thereby, some of the anchor groups must be adjusted, if necessary, to the chemical properties of the metal complexes to be linked. For some selected metals, such possibilities are shown in the following examples.

Example 12.1

Gold Complexes

Example for a gold emitter:

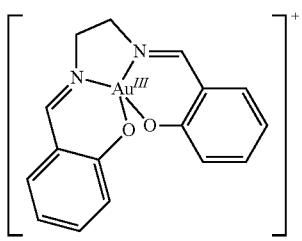

Unmodified, luminescent gold complex.
Orange colored luminescence (570 nm), see *Coord. Chem. Rev.* 2006, 250, 2093-2126

Example for a gold catalysis:

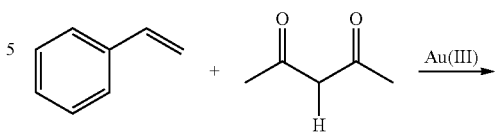

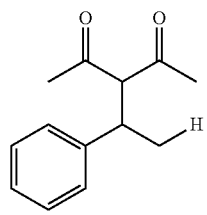

Catalytic example reaction, e.g. *Angew. Chem.*, 2005, 117, 7150

Anchor groups derived therefrom:

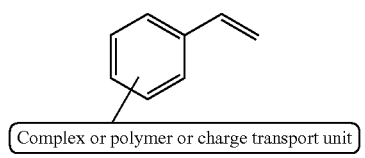

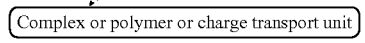

Modified complex derived therefrom:

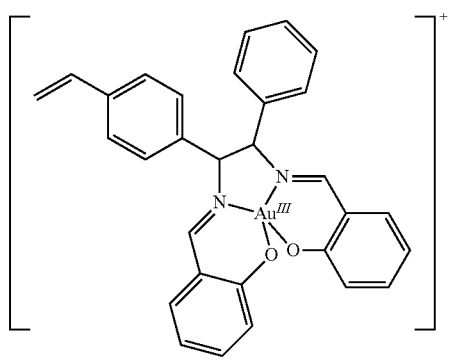

Example 12.2

Ruthenium Complexes

Ruthenium complexes also catalyze cycloadditions between alkynes and azides, but result in 1,5-triazoles in contrary to copper-catalyzed click reactions which result in 1,4-triazoles.

Example for a ruthenium emitter:

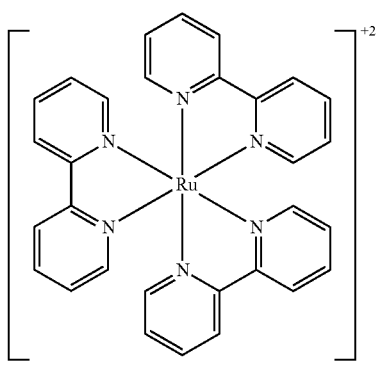

Unmodified, luminescent ruthenium complex.
Red luminescence (614 nm), see *Coord. Chem. Rev.* 2006, 250, 2093-2126

Example for a ruthenium catalysis:

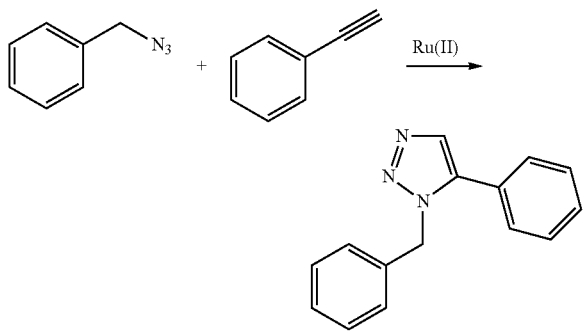

Catalytic example reaction, e.g. *J.Am. Soc.*, 2008, 130, 28, 8923-8930.

Anchor groups derived therefrom:

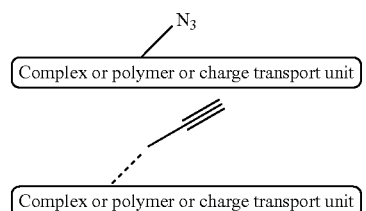

Modified complex derived therefrom:

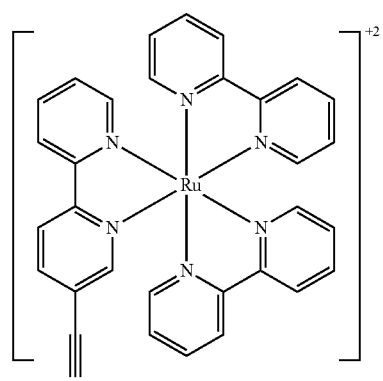

Example 12.3

Zinc Complexes

Example for a zinc emitter:

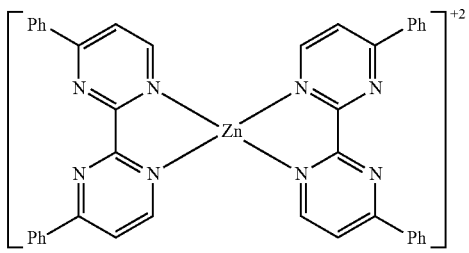

Unmodified, luminescent zinc complex.
Blue luminescence (415 nm), see *Coord. Chem. Rev.* 2006, 250, 2093-2126

Example for a zinc catalysis:

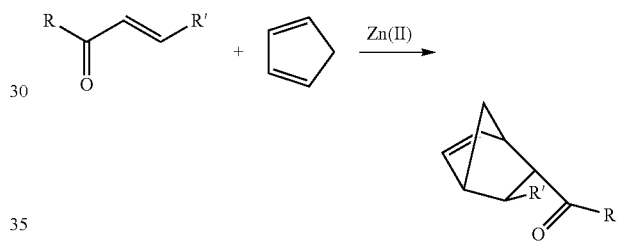

Catalytic example reaction, e.g. *Coord. Chem. Rev.*, 2000, 200-202, 717-772.

Anchor groups derived therefrom:

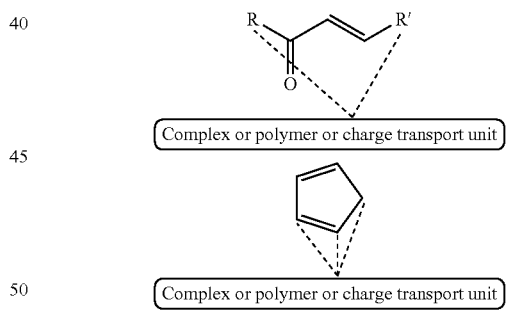

Modified complex derived therefrom:

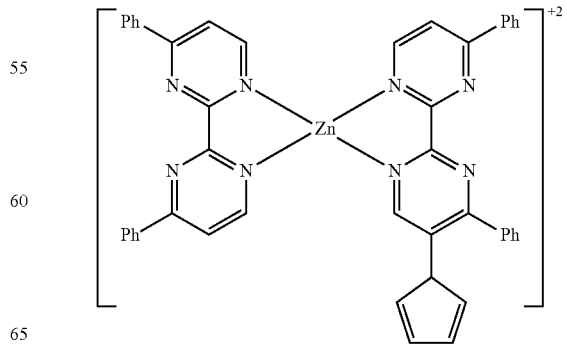

Example 12.4

Platinum Complexes

Example for a platinum emitter:

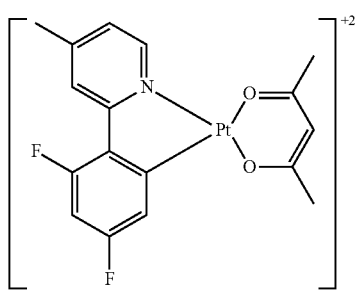

Unmodified, luminescent platinum complex.
See *J. Am. Soc.* 2004, 126, 47, 15388-15389

Example for a platinum catalysis:

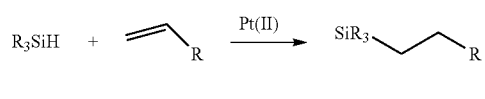

Catalytic example reaction, e.g. *J. Am. Soc.* 196, 108, 23, 7228-7231. (silanes) L. Pavasi, R. Turan, "*Silicon Nanocrystals: Fundamentals, Synthesis and Applications*", J. Viley, 2010, page 165 ff. (silicon nanoparticle)

Anchor groups derived therefrom:

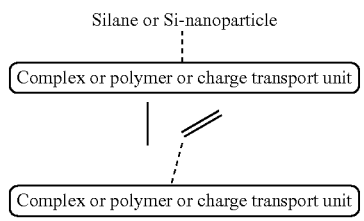

Modified complex derived therefrom:

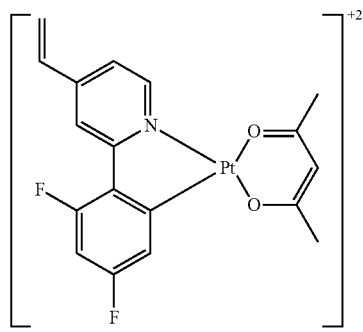

Example 11

Cross-linking of a Cu(I) complexes via a spacer molecule (third reactant) with a polymer.

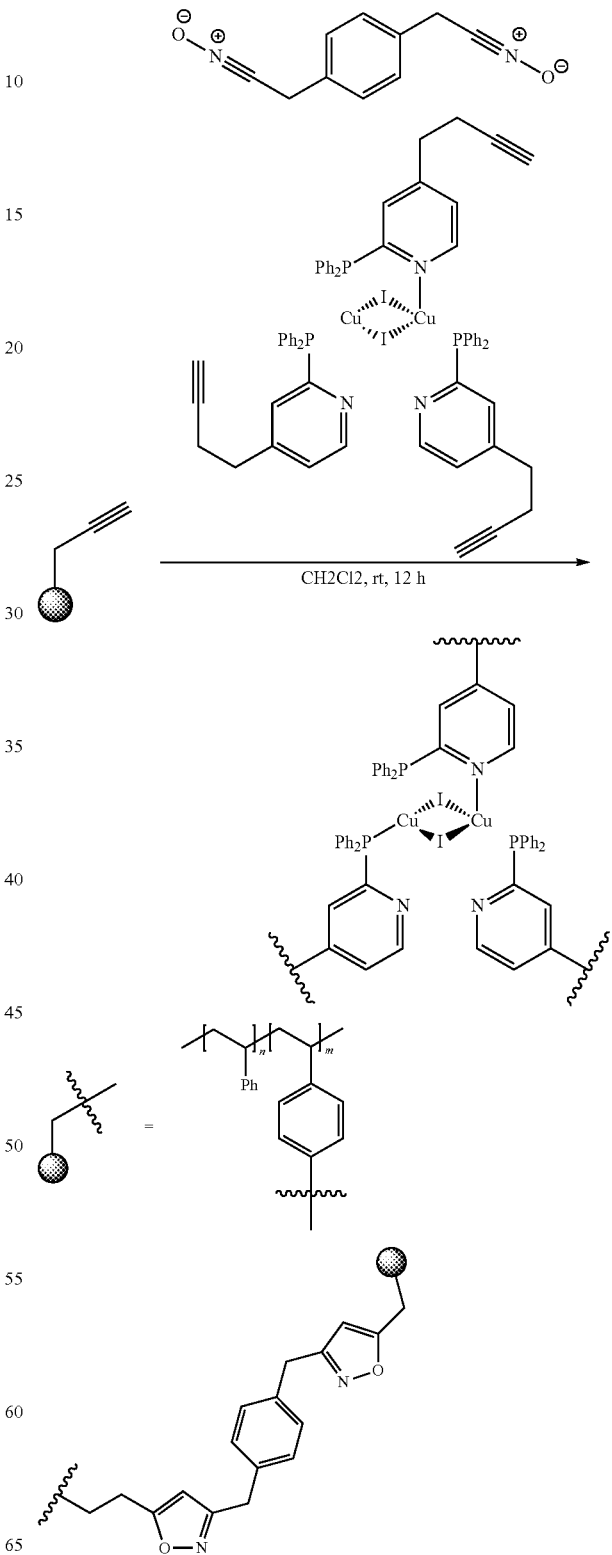

The invention claimed is:

1. A method for covalently bonding an organic metal complex with at least one metal center and at least one organic ligand to a polymer, comprising:
performing a first reaction, which comprises:
a first reactant in the form of the organic metal complex; and
a second reactant in the form of a polymer;
wherein the organic metal complex is covalently bound to the polymer during the first reaction;
wherein the first reaction is catalyzed by the metal center of the organic metal complex;
wherein the organic metal complex comprises an anchor group of a first anchor group species for covalently bonding the organic metal complex to the polymer;
wherein the second reactant comprises an anchor group of a second anchor group species for covalently bonding the second reactant to the organic metal complex;
wherein the covalent bonding of the organic metal complex to the polymer is achieved through a reaction of the anchor group of the organic metal complex with the anchor group of the second reactant;
wherein the first and the second anchor group species are selected from the corresponding pairs of the following first and second anchor group species:

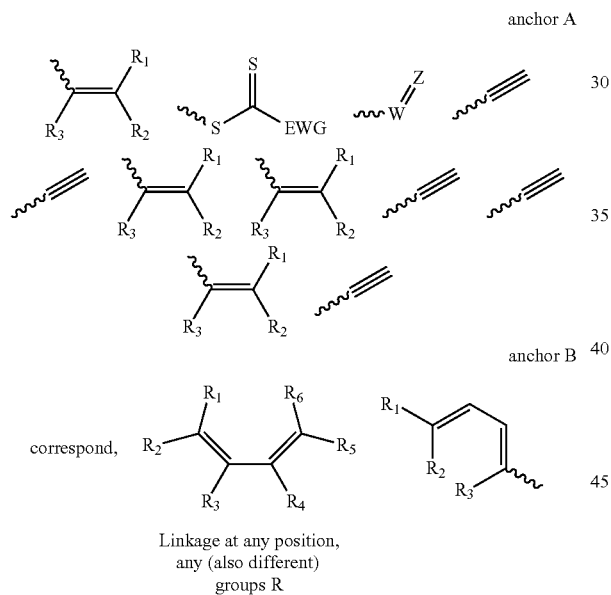

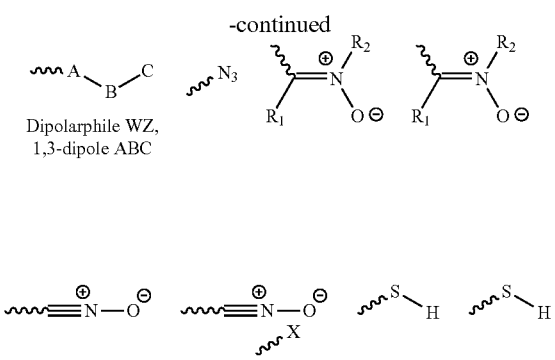

wherein:

EWG is an electron withdrawing group;

$R_1$-$R_6$ can each independently be hydrogen, a halogen or —OR*, —NR*$_2$ or —SiR*$_3$ as well as alkyl, aryl, heteroaryl, alkenyl, alkynyl groups or substituted alkyl, aryl, heteroaryl and alkenyl groups;

R*=an organic group selected from the group consisting of hydrogen, a halogen or deuterium, as well as alkyl, aryl, heteroaryl, alkenyl, and alkynyl groups or substituted alkyl, aryl, heteroaryl and alkenyl groups; and X=halogen, $OSO_2Me$, $OSO_2Tolyl$, or $OSO_2CF_3$.

2. The method according to claim 1, wherein the metal center of the organic metal complex is selected from the group consisting of Re, Fe, Ru, Os, Co, Rh, Ir, Ni, Pd, Pt, Cu, Ag, Au, Zn, Cd, Hg, Sn and Pb.

3. The method according to claim 1, wherein the polymer is used as an emitter or an absorber in an optoelectronic component.

4. An optoelectronic component, comprising the polymer of claim 1, wherein the optoelectronic component is selected from the group consisting of an organic light-emitting diodes (OLEDs), a light-emitting electrochemical cell (LEEC or LEC), an OLED-sensor, wherein the OLED sensor is a gas and vapor sensor which is not hermetically screened from the outside, an optical temperature sensor, an organic solar cell (OSC), an organic field-effect transistor, an organic diode, an organic photodiode and a down-conversion element.

5. The method according to claim 1, wherein $R_1$-$R_6$ optionally lead to annulated ring systems.

* * * * *